(12) United States Patent
Terakawa et al.

(10) Patent No.: US 7,346,245 B2
(45) Date of Patent: Mar. 18, 2008

(54) SWITCH-TYPE IMAGING FIBER APPARATUS AND BRANCH-TYPE IMAGING FIBER APPARATUS

(75) Inventors: Susumu Terakawa, Hamamatsu (JP);
Takashi Sakurai, Hamamatsu (JP);
Yoshihiko Wakazono, Hamamatsu (JP);
Hideo Hirukawa, Musashino (JP);
Takeo Tanaami, Musashino (JP)

(73) Assignees: National University Corporation, Hamamatsu University School of Medicine, Shizuoka (JP); Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 11/600,328

(22) Filed: Nov. 16, 2006

(65) Prior Publication Data

US 2007/0112256 A1    May 17, 2007

(30) Foreign Application Priority Data

Nov. 16, 2005   (JP)   ............................ 2005-331533
Nov. 16, 2005   (JP)   ............................ 2005-331860

(51) Int. Cl.
    *G02B 6/06*    (2006.01)
(52) U.S. Cl. ..................... 385/116; 600/178; 385/120
(58) Field of Classification Search ........ 385/115–120, 385/15; 607/80–88
    See application file for complete search history.

(56) References Cited

U.S. PATENT DOCUMENTS 4,279,247 A * 7/1981 Kinoshita ................... 600/103
5,619,370 A * 4/1997 Guinosso .................... 359/362
2002/0027708 A1* 3/2002 Lin et al. .................... 359/385
2003/0153825 A1* 8/2003 Mooradian et al. ......... 600/407
2004/0037554 A1* 2/2004 Ferguson et al. ............. 398/28

FOREIGN PATENT DOCUMENTS

| JP | 59-223079 | 12/1984 |
| JP | 10-260324 | 9/1998 |
| JP | 11-192204 | 7/1999 |

* cited by examiner

*Primary Examiner*—Frank G. Font
*Assistant Examiner*—Hung Lam
(74) *Attorney, Agent, or Firm*—Venable LLP; Michael A. Sartori; Steven J. Schwarz

(57) ABSTRACT

A switch-type imaging fiber apparatus and a branch-type imaging fiber apparatus are provided. Light emitted from a laser light source is made incident on an opening of an IF (image fiber) guided by a GM (galvanometer), output from an optical system provided at a leading end portion of the IF, and applied to an observation target. The light reflected by the observation target is sent back to the IF, transformed into parallel light by an fθ objective lens, reflected by a dichroic mirror, made incident on an image pickup device (CCD) via an imaging lens, and can be observed on a monitor. The GM is controlled to switch to make the light incident on the opening of an arbitrary one of a plurality of IFs. Accordingly, observation can be performed by focusing the light solely on the arbitrary IF.

6 Claims, 11 Drawing Sheets

FIG. 11

SWITCH-TYPE IMAGING FIBER APPARATUS AND BRANCH-TYPE IMAGING FIBER APPARATUS

BACKGROUND OF THE INVENTION

1. Field of the Invention

The present invention relates to a switch-type imaging fiber apparatus which inserts imaging fibers into a plurality of introduction holes formed in a biological body or the like and switches laser light or the like incident on end surfaces of the respective imaging fibers to thereby observe affected areas or the like located at the leading ends of the imaging fibers. The present invention also relates to a branch-type imaging fiber apparatus which inserts imaging fibers into a plurality of introduction holes drilled in a biological tissue or the like and allows or blocks the incidence of laser light or the like through an ON-OFF mechanism provided at end surfaces of the respective imaging fibers to thereby observe affected areas or the like located at the leading ends of the imaging fibers.

2. Description of the Related Art

A system has been in practical use which forms an introduction hole reaching an affected area of a biological body, inserts an imaging fiber into the introduction hole, applies light to the affected area from the leading end of each of the imaging fiber, and receives reflected light from the affected area to thereby observe the affected area with a microscope, a monitor, or the like.

To cope with a case in which a multitude of affected areas exist, a corresponding apparatus is provided which individually makes the light incident on a plurality of imaging fibers to observe the affected areas. In this case, separate endoscope devices need to be provided to form the respective imaging fibers. Thus, the size of the apparatus is increased and the operation of the apparatus becomes complicated, which is inefficient. Further, in a case in which treatments or the like are performed on the affected areas, i.e., the observation targets existing at a plurality of locations, and the process of and the causal relationship between the treatments or the like are examined, the above configuration is inconvenient to view the observation images obtained by the respective imaging fibers in terms of the chronological change.

Examples of a fiber apparatus using a multitude of optical fibers for observation are disclosed in Japanese Unexamined Patent Application Publication No. 11-192204 and Japanese Unexamined Patent Application Publication No. 10-260324, for example.

The former apparatus relates to an intestinal endoscope, in which inner end portions of a multitude of objective fiberscopes 10 are divided into two rows and disposed in proximity to each other on a straight line. Then, a leading end portion of an image transmission fiber cable 15 is disposed in the longitudinal direction in proximity to the inner ends of the fiberscopes 10. The leading end of the cable 15 is attached with a prism 16, while a pinion 20 and a rack 18, which are driven by a micro motor 19, are provided at a rear position of the cable 15. The leading end portion of the cable 15 is then caused to perform a reciprocating movement in the longitudinal direction, and images transmitted by the prism 16 to the inner ends of the respective fiberscopes 10 are sequentially transferred to the image transmission fiber cable 15 and displayed on a monitor. However, the above proposal is for observing the inner wall of the intestinal tract with the multitude of objective fiberscopes 10, and is not the apparatus for observing, substantially at the same time, a multitude of affected areas positioned apart from one another in a biological body.

According to the latter apparatus, images captured by a multitude of objective lenses 201 to 209 provided at the front, rear, and side positions of a vehicle are transmitted to ocular lenses 221 to 229 by optical fibers 211 to 219. Then, as a reflecting mirror 23 is driven by a servo motor 24, the images sent from the ocular lenses 221 to 229 are guided to a photoelectric element 25 through optical scanning, converted into electrical signals, and sent to a control and monitor unit 26.

According to the above proposal, however, the multitude of fibers are provided at the front, rear, and side positions of the vehicle, and image information captured by the objective lens 201 to 209 is sequentially scanned by the reflecting mirror 23 to thereby display the light incident on a plurality of image guides on a monitor screen. Thus, the above proposal is not for applying light to observation targets from the respective fibers and receiving resultant reflected light. Therefore, the apparatus is not provided with a portion including a light source and a switching mechanism for making the light enter into or exit from the respective fibers at a bundled part of the image guides. Further, the fibers cannot be used as fibers for observing respective affected areas in a biological body.

Furthermore, Japanese Unexamined Patent Application Publication No. 59-223079 discloses an apparatus which displays on a monitor an image obtained by the leading ends of a plurality of fibers bundled together. The above apparatus is an image transmission apparatus having a plurality of (e.g., four) branch image guides, which are bundled together at an image receiving side and connected to an image receiving unit of a television camera, to thereby display a cross-patterned image including four divided rectangular images on a monitor screen 5. The apparatus is for displaying the light incident on the plurality of image guides on the monitor screen, and not for applying light to observation targets from the respective fibers and receiving resultant reflected light. Therefore, the apparatus is not provided with a portion including a light source and a ON-OFF mechanism for making the light enter into or exit from the respective fibers at a bundled part of the image guides. Further, the fibers cannot be used as fibers for observing respective affected areas in a biological body.

SUMMARY OF THE INVENTION

The present invention is mainly based on the assumption that a plurality of fibers (endoscopes) are inserted in a biological body. A first object of the present invention is to provide a switch-type imaging fiber apparatus in which the incidence of light on and the detection of light in the plurality of fibers are controlled to be switched by the single apparatus to enable chronological observation of the states of a multitude of affected areas in a biological body, without increasing the size of the apparatus and by a simple switching operation.

A second object of the present invention is to provide a branch-type imaging fiber apparatus in which the incidence of light on and the detection of light in the plurality of fibers are ON-OFF controlled by the single apparatus to enable simultaneous and chronological observation of a multitude of affected areas in a biological body, without increasing the size of the apparatus and by a simple operation.

To achieve the first object, a switch-type imaging fiber apparatus according to a first aspect of the present invention applies light to an observation target from a leading end thereof and receives resultant reflected light, and is used to observe a biological body. The switch-type imaging fiber apparatus includes a plurality of imaging fibers, a light source device, a movable mirror unit, an objective lens system, and an optical unit. Each of the plurality of imaging fibers includes an optical system at a leading end portion thereof to apply the light to the observation target. The movable mirror unit changes the traveling direction of light emitted from the light source device. The objective lens system focuses the light emitted from the light source device so as to form an irradiation surface approximately the same in area as an end surface of one of the plurality of imaging fibers. The optical unit forms an image on an image pickup device from the reflected light reflected by the measured target and obtained through the objective lens system and the imaging fiber. As the movable mirror unit is driven, the light emitted from the light source device is switched to be made incident among the end surfaces of the plurality of imaging fibers.

According to a second aspect of the present invention, in the switch-type imaging fiber apparatus according to the first aspect, the movable mirror unit may be one of a polygon mirror and a GLV (grating light valve), which changes the traveling direction of the light incident on the objective lens system.

According to a third aspect of the present invention, in the switch-type imaging fiber apparatus according to the first aspect, the movable mirror unit may be one of a GM (galvanometer), a DMD (digital micromirror device), and an AOM (acoustic optical modulator), which changes the traveling direction of the light incident on the objective lens system.

According to a fourth aspect of the present invention, a switch-type imaging fiber apparatus applies light to an observation target from a leading end thereof and receives resultant reflected light, and is used to observe a biological body, for example. The switch-type imaging fiber apparatus includes a plurality of imaging fibers, a moving unit for fixing end surfaces of the plurality of imaging fibers at predetermined intervals and capable of causing one of rotation and linear movement of the end surfaces, a light source device, and an objective lens system for focusing light emitted from the light source device so as to form an irradiation surface approximately the same in area as the end surface of one of the plurality of imaging fibers. As the moving unit is driven to move the end surface of the imaging fiber, the light emitted from the light source device is switched to be made incident among the end surfaces of the plurality of imaging fibers.

According to a fifth aspect of the present invention, in the switch-type imaging fiber apparatus according to the fourth aspect, the moving unit may be formed into one of a rotary revolver system in which the end surfaces of the plurality of imaging fibers are circumferentially arranged and rotated, a belt conveyance system in which the end surfaces of the plurality of imaging fibers are attached to a belt in a row and the belt is driven, and an IF (image fiber) array rotation system in which the end surfaces of the plurality of imaging fibers are arranged in an array and rotated.

According to a sixth aspect of the present invention, in the switch-type imaging fiber apparatus according to the fifth aspect, each of the imaging fibers may be formed by a few thousands to a few tens of thousands of fiber strands.

To achieve the second object, according to a seventh aspect of the present invention, a branch-type imaging fiber apparatus applies light to an observation target from a leading end thereof and receives resultant reflected light, and is used to observe a biological body. In the branch-type imaging fiber apparatus, a single imaging fiber is branched into a plurality of branch imaging fibers, each of which has the leading end attached with an optical system to apply the light to the observation target, and an end surface formed into a hexagonal shape. The branch-type imaging fiber apparatus includes a light source device, an objective lens system for focusing light emitted from the light source device so as to apply the light to the entirety of the end surfaces of the plurality of branch imaging fibers, and a light path blocking mechanism for covering the entirety of the end surfaces of the plurality of branch imaging fibers. The light path blocking mechanism individually performs a blocking control on the respective end surfaces of the branch imaging fibers.

According to an eighth aspect of the present invention, in the branch-type imaging fiber apparatus according to the seventh aspect, the light path blocking mechanism may be formed by a crystal shutter.

According to a ninth aspect of the present invention, in the branch-type imaging fiber apparatus according to the eighth aspect, each of the branch imaging fibers may be formed by a few thousands to a few tens of thousands of fiber strands.

According to the configurations of the first to sixth aspects of the present invention, the states of a multitude of affected areas in a biological body can be chronologically observed, without increasing the size of the apparatus and by a simple switching operation. Further, it is possible to make the number of the IFs unlimited, and to focus the light to be switched on one of the IFs. If the GLV is employed, the IFs can be separated by color.

According to the configurations of the seventh to ninth aspects of the present invention, even if the number of the imaging fibers is large, the structure of the apparatus can be made simple. Accordingly, it is possible to reduce the size of the apparatus and switch the light at a high speed.

The switch-type imaging fiber apparatus and the branch-type imaging fiber apparatus are in common in that the both apparatuses enable chronological observation of the states of the multitude of affected areas in the biological body, without increasing the size of the apparatuses. The switch-type imaging fiber apparatus switches all of the light to be input and supplies the switched light to each of the image fiber devices, and thus can make a larger amount of light incident on the respective imaging fibers than the branch-type imaging fiber apparatus does. Meanwhile, the branch-type imaging fiber apparatus divides the light and makes the divided lights incident on the respective imaging fibers. Thus, the amount of the light incident on the respective imaging fibers is smaller than in the switch-type imaging fiber apparatus. However, the branch-type imaging fiber apparatus can employ the crystal shutter as the structure for dividing the light, and thus is advantageous over the switch-type imaging fiber apparatus in terms of further reduction in size of the apparatus.

DESCRIPTION OF THE PREFERRED EMBODIMENTS

Embodiments of the present invention will now be described in detail with reference to the drawings.

Figure 1:
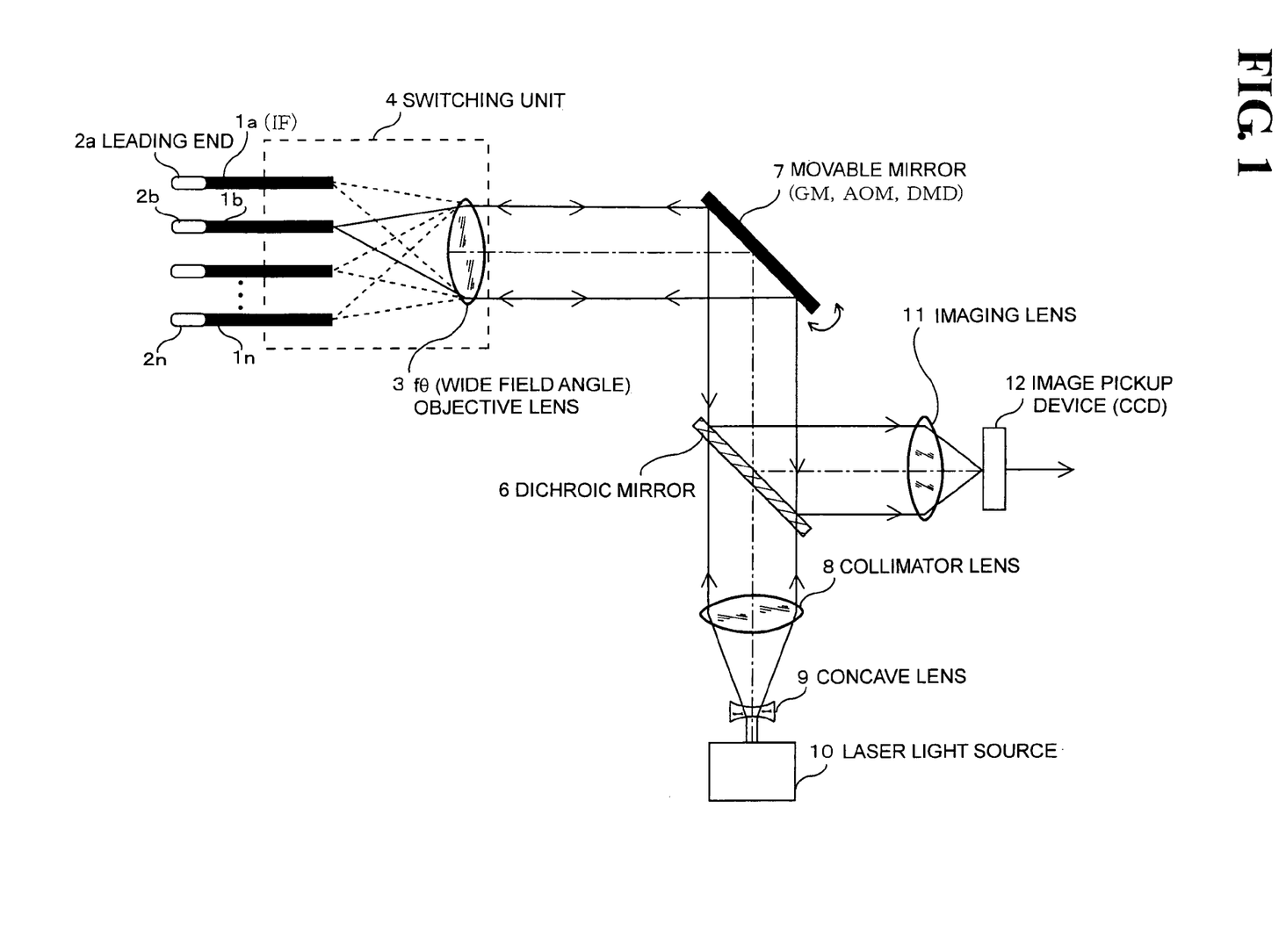
FIG. 1 is a schematic diagram illustrating an embodiment of a switch-type imaging fiber apparatus according to the present invention, in which a movable mirror is employed.

FIG. 1 is a schematic diagram illustrating an embodiment of a switch-type imaging fiber apparatus according to the present invention. The present embodiment uses an optical switching system and employs a movable mirror, which is a GM (galvanometer) in the present example.

Reference numerals $1a$ to $1n$ indicate imaging fibers (hereinafter referred to as the "IFs"). Each of leading end portions $2a$ to $2n$ is attached with an optical system for applying light to an observation target and taking in resultant reflected light. The other end of each of the IFs $1a$ to $1n$ is formed with an opening for taking in the light, and is disposed at a predetermined position within a switching unit 4. Each of the IFs $1a$ to $1n$ is formed by bundling together a multitude of optical fiber strands, and has predetermined elasticity (i.e., flexibility), capable of being bent with a curvature set so as not to be equal to or smaller than a predetermined value.

Laser light sent out from a laser light source 10 is diffused by a concave lens 9 and made incident on a collimator lens 8. The diffused light is transformed into parallel light by the collimator lens 8, transmitted through a dichroic mirror 6, switched by a movable mirror 7, converged by an fθ objective lens 3, and made incident on the opening of one of the IFs $1a$ to $1n$ to which the light has been switched.

The light made incident on the opening reaches the optical system located at the leading end portion via the multitude of optical fiber strands. As the light emitted from the optical system hits the observation target, light (e.g., fluorescent light) is generated. The generated light returns back to the opening via the optical system.

The light output from the opening is transformed into parallel light by the fθ objective lens 3, switched by the movable mirror 7, reflected by the dichroic mirror 6, and made incident on an image pickup device (CCD) 12 via an imaging lens 11. The light is then converted into an electrical signal by the image pickup device 12, and the converted electrical signal is guided to an image pickup device control unit. By controlling to switch the movable mirror 7 to make the light incident on the opening of an arbitrary one of the plurality of IFs, observation can be performed by focusing the light solely on the arbitrary IF. As well as the method described above, a water lens, for example, can be employed as the movable mirror according to the present embodiment for controlling the field angle. Further, the switching can be similarly performed by employing a polygon mirror or a GLV (grating light valve).

Figure 2:
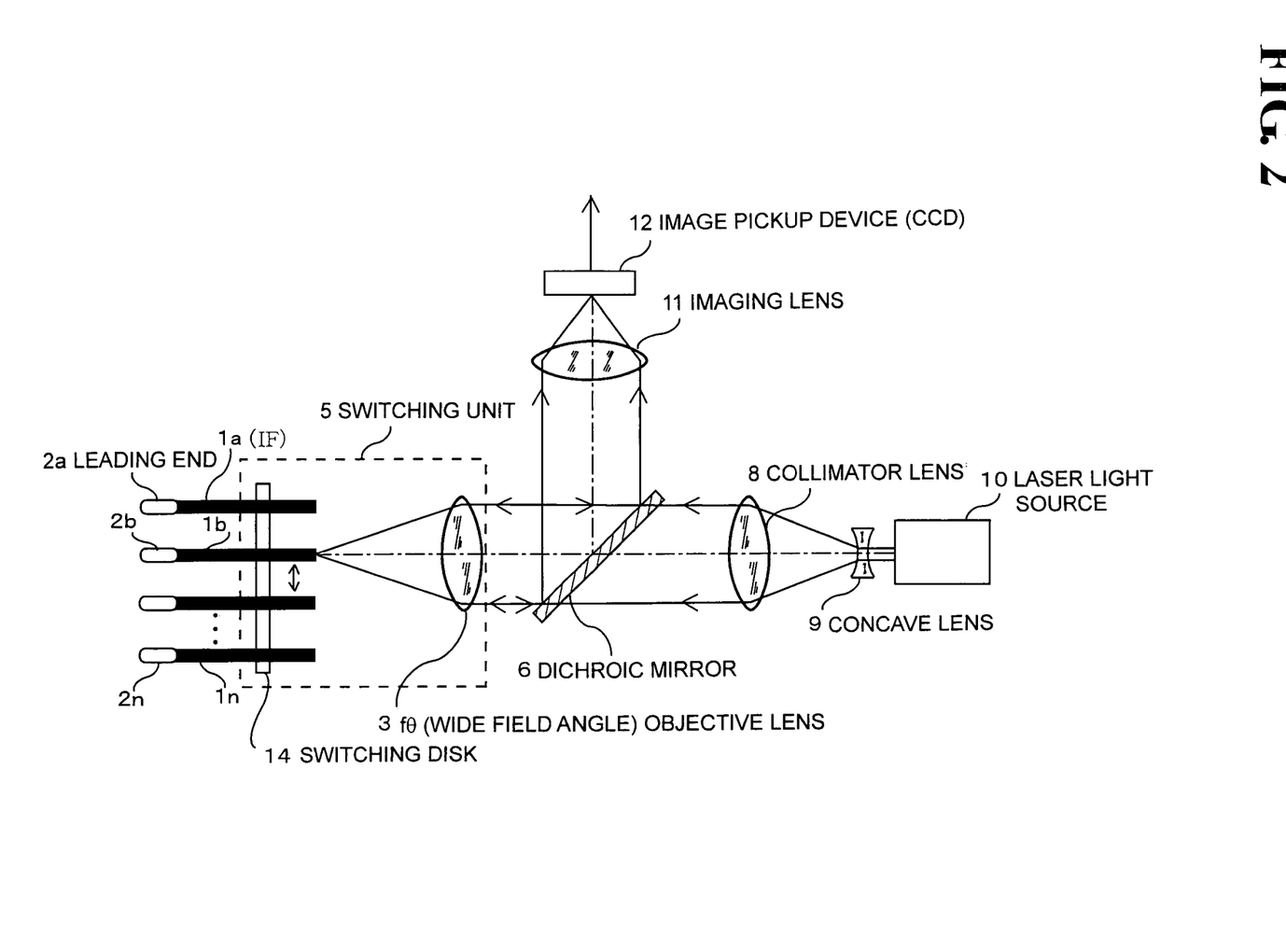
FIG. 2 is a schematic diagram illustrating another embodiment of the switch-type imaging fiber apparatus according to the present invention, in which a switching disk is employed.

FIG. 2 is a schematic diagram illustrating another embodiment of the switch-type imaging fiber apparatus according to the present invention. The present embodiment uses a mechanical switching system and employs a switching disk. The configuration of each of the imaging fibers $1a$ to $1n$, and the configuration and the arrangement of each of the collimator lens 8, the dichroic mirror 6, the fθ objective lens 3, the imaging lens 11, and the image pickup device 12 are the same as in FIG. 1. Thus, description thereof will be omitted. The opening formed at the other end of each of the IFs $1a$ to $1n$ is supported by a switching disk 14.

Laser light output from the laser light source 10 is diffused by the concave lens 9 and made incident on the collimator lens 8. The diffused light is transformed into parallel light by the collimator lens 8, transmitted through the dichroic mirror 6, converged by the fθ objective lens 3, and made incident on the opening of an arbitrary one of the IFs. By performing switching control with the switching disk 14 to make the light incident on the opening of the arbitrary one of the plurality of IFs, observation can be performed by focusing the light solely on the arbitrary IF. As well as the above switching disk, a belt conveyance system or an IF array rotation system can be employed as the mechanical switching system.

Figure 3:
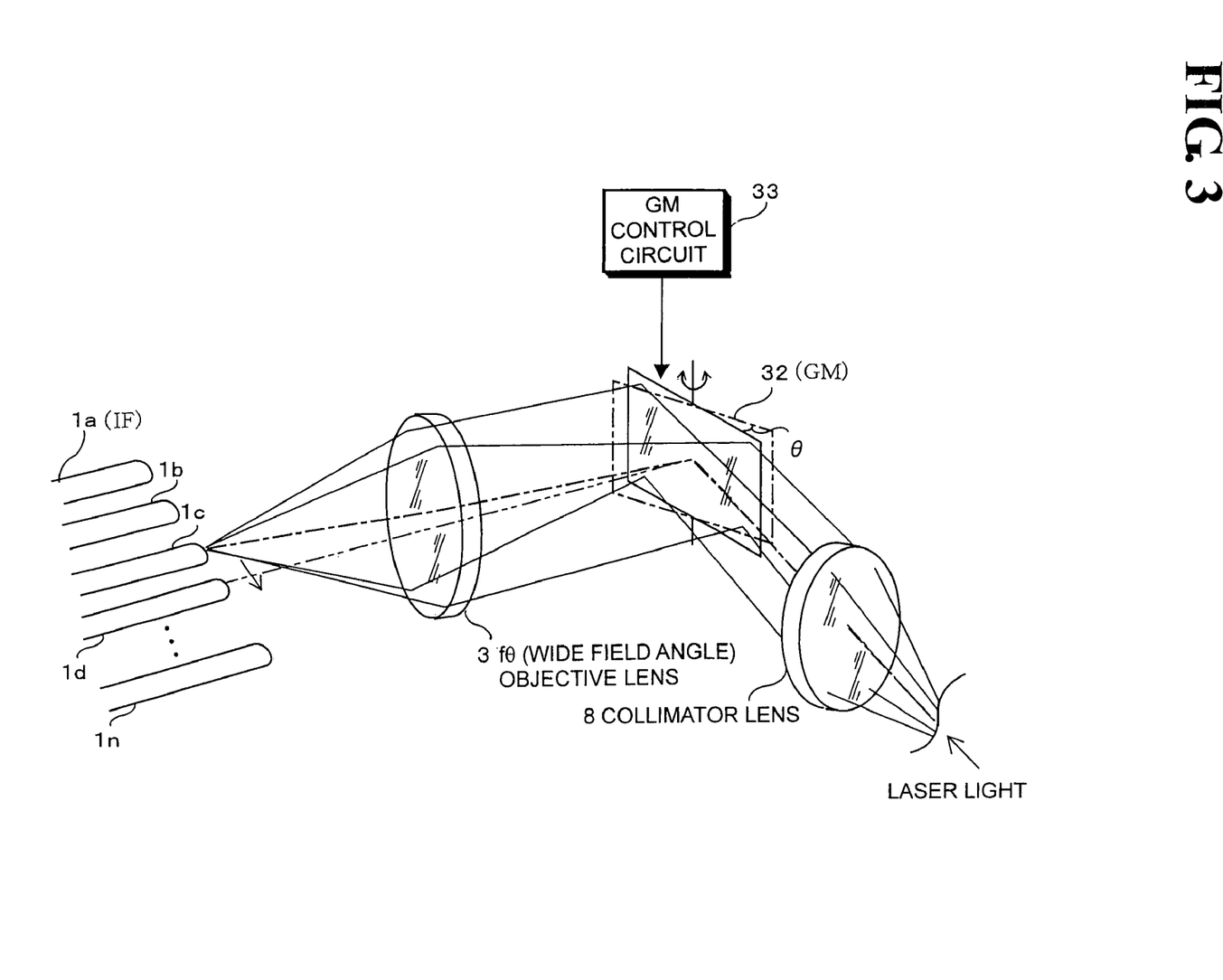
FIG. 3 is a diagram illustrating details of a GM device.

FIG. 3 is a diagram illustrating details of the above GM device, in which an observation optical system including the dichroic mirror is omitted. A GM control circuit 33 controls a GM 32 to rotate to an angle corresponding to the position of the opening of one of the IFs $1a$ to $1n$. The light emitted from the light source is converged into the parallel light by the collimator lens 8, reflected by the GM 32, converged by the fθ objective lens 3, and made incident on the opening of the IF.

The present example illustrates the state in which the light is incident on the IF $1c$. To switch to the IF $1d$, for example, the GM control circuit 33 controls the GM 32 to rotate by an angle θ to thereby make the light incident on the IF $1d$. Further, to switch to another one of the IFs, the angle of the GM 32 is controlled to be equal to an angle corresponding to the IF. Thereby, the switching among the IFs can be performed sequentially or at random.

Figure 4:
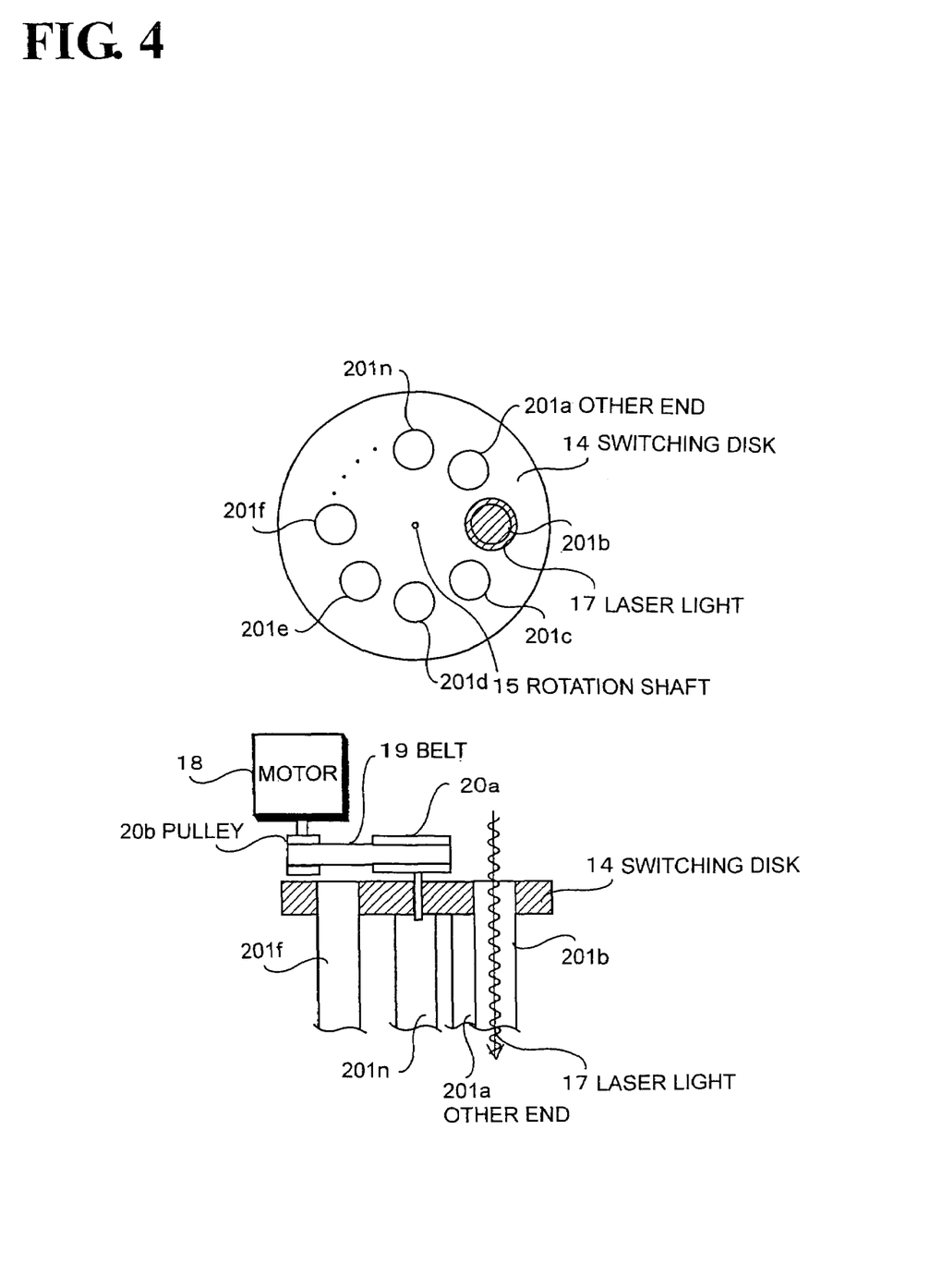
FIG. 4 is a diagram illustrating details of a rotary revolver system.

FIG. 4 is a diagram illustrating details of a rotary revolver system. The openings formed at the other end portions $201a$ to $201n$ of the IF $1a$ to $1n$ are fixed along the circumference of the switching disk 14 at equal intervals such that the focused light can be made incident on the respective openings. A rotation shaft 15 is fixed to the center of the switching disk 14, and the leading end of the rotation shaft 15 is attached with a pulley $20a$. Another pulley $20b$ is fixed to an output shaft of a motor 18, and a belt 19 is stretched between the pulleys $20a$ and $20b$. As the motor 18 rotates, the switching disk 14 is driven to move. The diameter of the pulley $20a$ is set to be larger than the diameter of the pulley $20b$. Thus, the rotation of the motor 18 is transmitted to the switching disk 14 at a reduced speed.

In the present example, the focused light is set to be applied to a right outer circumferential portion of the switching disk 14. As the motor 18 rotates, the opening formed at the other end portion 201b of the IF 1b is set at the irradiation position, and laser light 17 is made incident on the IF 1b. The switching disk 14 is controlled to rotate by an angle not exceeding 180 degrees in the clockwise direction or in the counterclockwise direction to enable the switching to all of the IFs. If the switching disk 14 rotates by 180 degrees in the clockwise direction or in the counterclockwise direction, the IFs 1a to 1n are bent, but the material forming the IFs 1a to 1n is flexible, i.e., the material has flexibility. Therefore, a mechanical trouble is prevented, as long as the rotation angle is within the above range.

Figure 5:
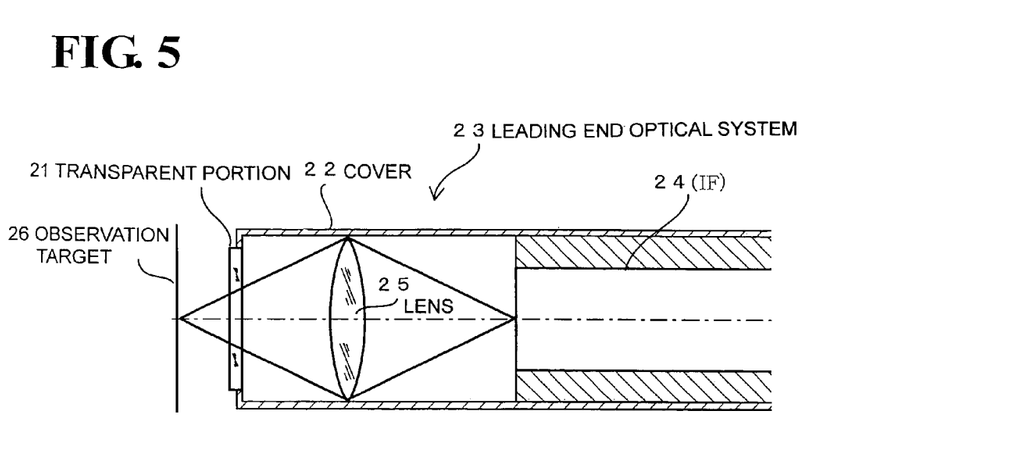
FIG. 5 is a diagram illustrating an example of an optical system provided at the leading end of each of imaging fibers.

FIG. 5 is a diagram illustrating a configuration of the optical system provided at the leading end portion of each of the imaging fibers. An IF 24 formed by bundled strands is stored in a cover 22, and a lens 25 is disposed at the leading end of the cover 22. The leading end of the cover 22 is attached with and sealed by a transparent portion 21. The light output from the leading end of the IF 24 is converged by the lens 25, transmitted through the transparent portion 21, and applied to an observation target 26. A biological body has been injected with a fluorescent liquid agent. Thus, when light of a predetermined wavelength is applied to the observation target 26, fluorescent light is emitted. The fluorescent light is converged by the lens 25 and made incident on the IF 24 to return to the observation optical system.

Figure 6:
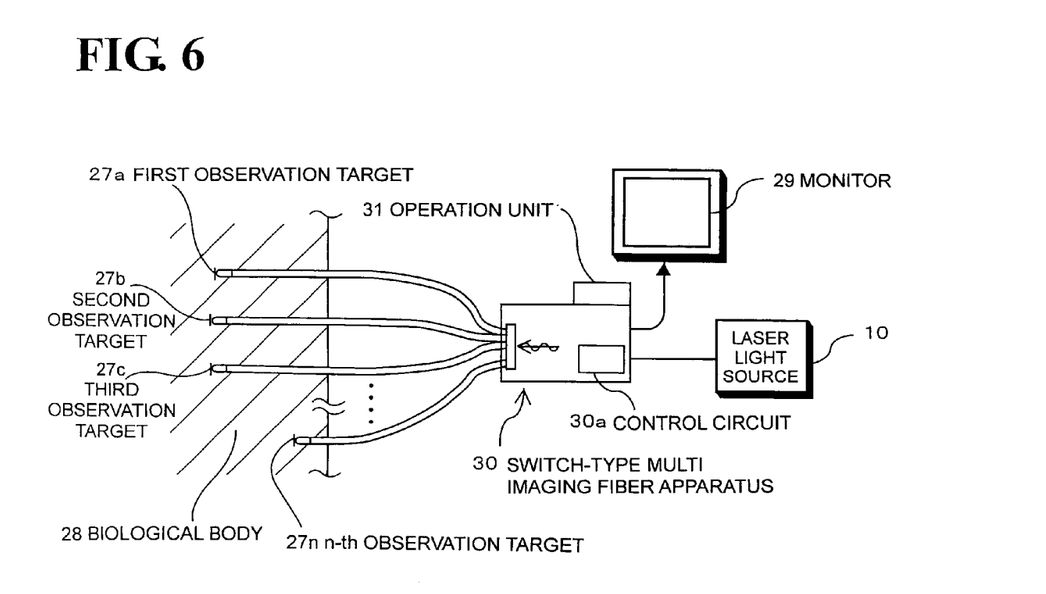
FIG. 6 is a diagram for explaining an embodiment of the use of the switch-type imaging fiber apparatus according to the present invention.

FIG. 6 is a diagram for explaining a use state of the switch-type imaging fiber apparatus according to the present invention. A switch-type multi imaging fiber apparatus 30 stores the opening formed at the other end of each of the IFs, and includes therein the fθ objective lens 3, the dichroic mirror 6, the collimator lens 8, the concave lens 9, the imaging lens 11, the image pickup device (CCD) 12, and so forth. The output of the image pickup device 12 is connected to the image pickup device control unit provided in a control circuit 30a. Further, the switch-type multi imaging fiber apparatus 30 is connected to the laser light source 10 by an optical waveguide to guide the laser light to the concave lens 9. The switch-type multi imaging fiber apparatus 30 is further connected to a monitor 29.

The operation unit 31 includes a button switch, a slide switch, and so forth, and an operation signal output from the operation unit 31 is sent to the control circuit 30a. The control circuit 30a is a circuit for controlling the entirety of the switch-type multi imaging fiber apparatus 30. If the movable mirror is the GM, the control circuit 30a includes the GM control circuit 33. On the basis of the operation signal, the control circuit 30a performs an ON-OFF control of the monitor 29 and the laser light source 10, and controls the image display range of the monitor 29. Further, on the basis of a specification signal for specifying the IF which should be supplied with the light, the control circuit 30a controls to rotate the GM 32 to switch to the opening of the specified IF.

The monitor 29 can display, on a part or the entirety of the screen thereof, the image corresponding to the specified IF, and can similarly display the image corresponding to another IF through the switching control. Accordingly, the multiple-point measurement can be performed by the single switch-type multi imaging fiber apparatus 30. The present example illustrates the state in which a biological body 28 is formed with holes at a plurality of (e.g., six) locations, and the IFs are inserted in the holes. Further, the light is applied to the first to n-th observation targets 27a to 27n, and the light emitted from the respective observation targets is received and image-processed by the image pickup device 12. Then, the image of the observation target of the specified IF is selected by switching and observed on a part or the entirety of the screen of the monitor 29.

The embodiment of FIG. 6 illustrates the example in which the plurality of locations in the biological body are observed by the single apparatus. It is also possible to observe an observation target existing at one location from different angles. In the present switch-type imaging fiber apparatus, it is possible to make the number of the IFs unlimited, and to measure the respective observation targets by focusing the light to each of the IFs and switching among IFs sequentially or at random.

In the embodiments described above, the GM is used as an example of the optical switching system. As well as the GM, an AOM (acoustic optical modulator) or a DMD (digital micromirror device) can be employed to switch the angle. Further, the polygon mirror or the GLV can be employed. If the GLV is employed, the IFs can be separated by color. Furthermore, in the embodiments described above, the rotary revolver system is used as an example of the mechanical switching system. Alternatively, the belt conveyance system or the IF array rotation system can be employed.

Embodiments of a branch-type imaging fiber apparatus will now be described.

Figure 7:
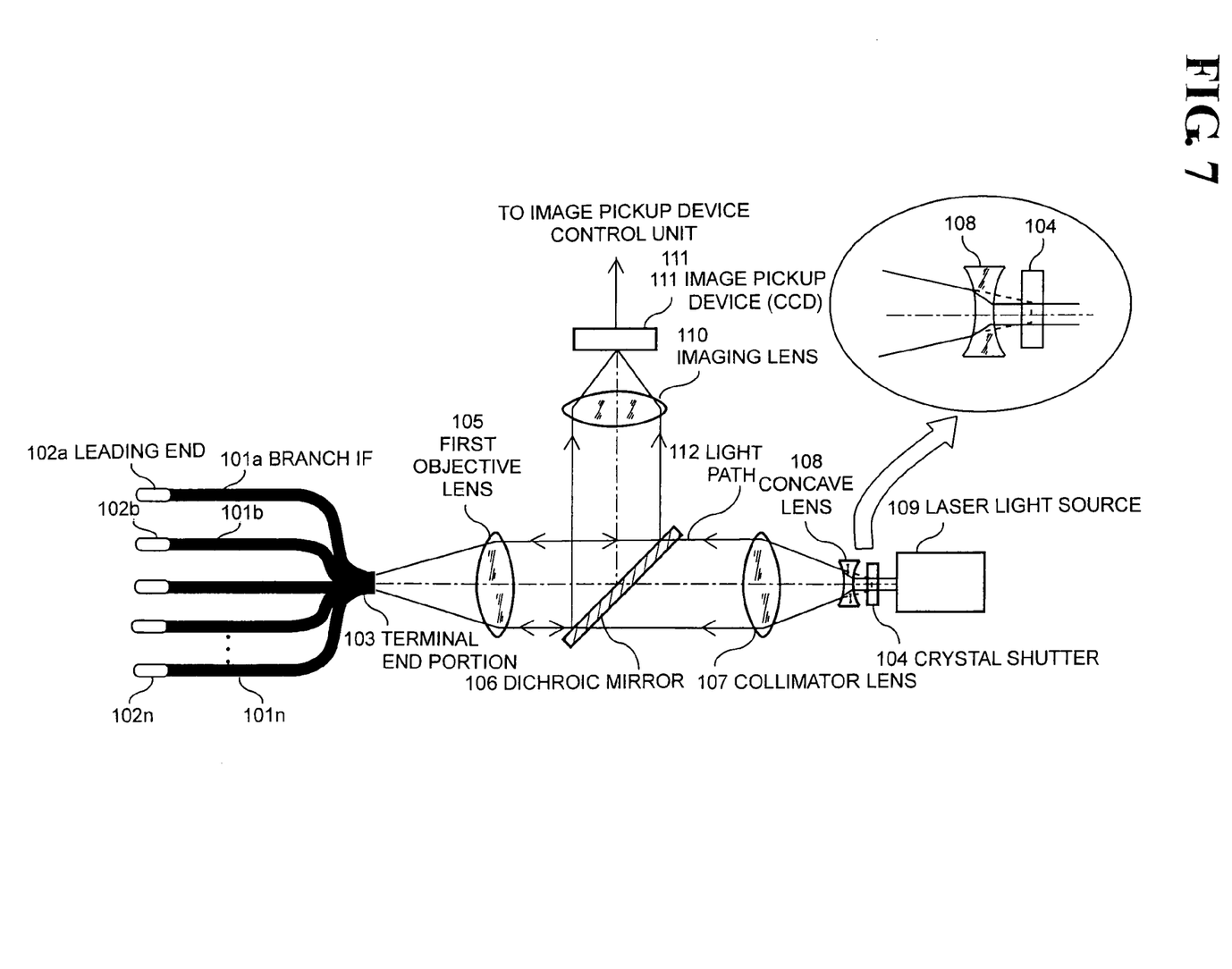
FIG. 7 is a schematic diagram illustrating an embodiment of a branch-type imaging fiber apparatus according to the present invention, in which a crystal shutter is employed.

FIG. 7 is a schematic diagram illustrating an embodiment of a branch-type imaging fiber apparatus according to the present invention, in which a crystal shutter is employed. Reference numerals 101a to 101n indicate branch imaging fibers (hereinafter referred to as the "branch IFs") formed by branching a single imaging fiber into, for example, approximately seven segments. Each of leading end portions 102a to 102n is attached with an optical system for applying light to an observation target and taking in resultant reflected light. A terminal end portion 103 of the branch IFs 101a to 101n is an integrated portion, and each of the branch IFs 101a to 101n is formed with an opening for taking in the light. Each of the branch IFs 101a to 101n is formed by bundling together a multitude of optical fiber strands, and has predetermined elasticity (i.e., flexibility), capable of being bent with a curvature set so as not to be equal to or smaller than a predetermined value.

Laser light sent out from a laser light source 109 is transmitted through a crystal shutter 104, diffused by a concave lens 108, and made incident on a collimator lens 107. The diffused light is transformed into parallel light by the collimator lens 107, transmitted through a dichroic mirror 106, and converged by a first objective lens 105 to form an irradiation surface incident on the openings of all of the branch IFs 101a to 101n of the terminal end portion 103. The crystal shutter 104 and the terminal end portion 103 are set to be in the optically conjugate positional relationship to each other.

The light incident on each of the openings reaches the optical system provided at the corresponding leading end portion via the multitude of optical fiber strands. As the light emitted from the optical system hits the corresponding observation target, light (e.g., fluorescent light) is generated. The generated light returns back to the opening via the optical system.

The light output from the terminal end portion 103 is transformed into parallel light by the first objective lens 105, reflected by the dichroic mirror 106, and made incident on an image pickup device (CCD) 111 via an imaging lens 110. The light is then converted into an electrical signal by the image pickup device 111, and the converted electrical signal is guided to an image pickup device control unit.

By opening and closing the crystal shutter 104 to transmit the light directed to a particular one of the branch IFs and to block the light directed to the other branch IFs, observation can be performed by applying the light solely to the particular branch IF. Further, observation through a multitude of branch IFs can be performed by simultaneously performing an ON control on the multitude of branch IFs.

Figure 8:
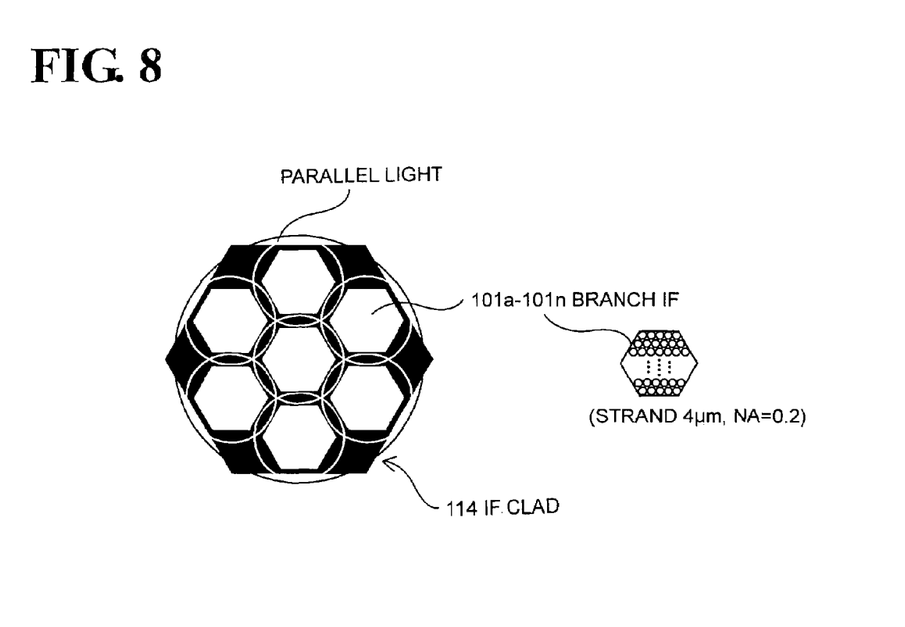
FIG. 8 is a diagram for explaining the shape of an end surface of a branch imaging fiber.

FIG. 8 is a diagram for explaining the shape of an end surface of each of the branch imaging fibers. Since the actual total number of the fiber strands is only a few tens of thousands, i.e., the number is limited, the number of the branch IFs cannot be increased much. The minimum number of the strands included in each of the branch IFs required to form a natural image is approximately 6000. Therefore, the maximum number of the segments to be formed is seven to eight. Further, the amount of light for each of the branch IFs is the amount obtained by simply dividing the original amount of light by the number of the segments. Thus, if the number of the segments is increased, the amount of light for each of the branch IFs is decreased. Therefore, the laser light source 109 needs to emit intense light.

It is efficient to form the bundled fiber strands, each of which is a few microns in diameter, into a regular hexagonal shape, since the area loss is not caused among the respective branch IFs. The lens-focused light is made incident on the entirety of the terminal end portion 103. The leading end portion is approximately a few millimeters in diameter size, and is attached with a mini lens 118 for focusing the light, as illustrated in FIG. 9.

Figure 9:
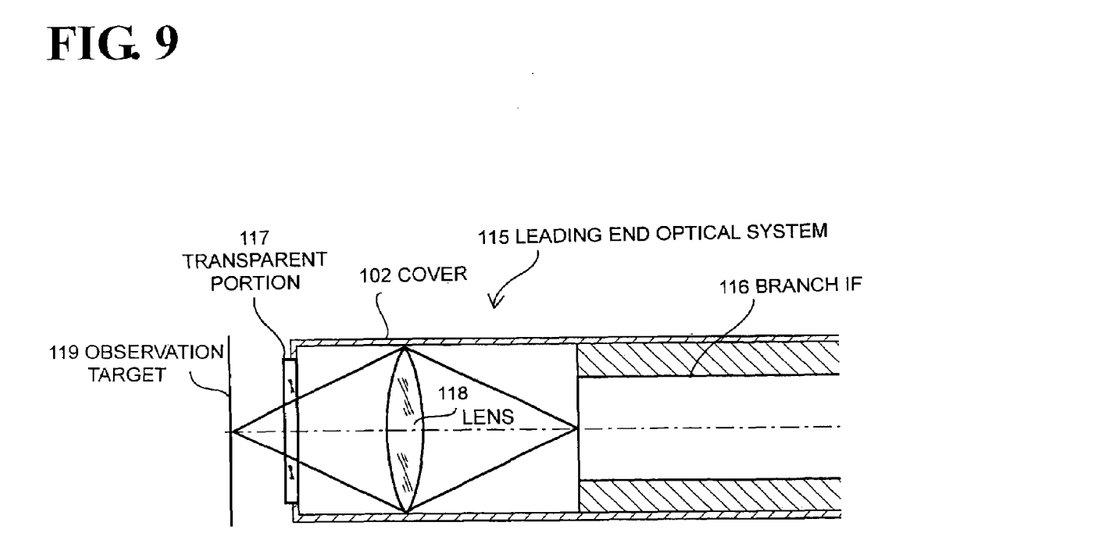
FIG. 9 is a diagram illustrating a configuration of an optical system provided at a leading end portion of the branch imaging fiber.

FIG. 9 is a diagram illustrating a configuration of the optical system provided at the leading end portion of one of the branch imaging fibers. A branch IF 116 formed by bundled strands is stored in a cover 102, and the lens 118 is disposed at the leading end of the cover 102. The leading end of the cover 102 is attached with and sealed by a transparent portion 117. The light output from the leading end of the branch IF 116 is converged by the lens 118, transmitted through the transparent portion 117, and applied to an observation target 119. A biological body has been injected with a fluorescent liquid agent. Thus, when light of a predetermined wavelength is applied to the observation target 119, fluorescent light is emitted. The fluorescent light is converged by the lens 118 and made incident on the branch IF 116 to return to the observation optical system.

Figure 10A:
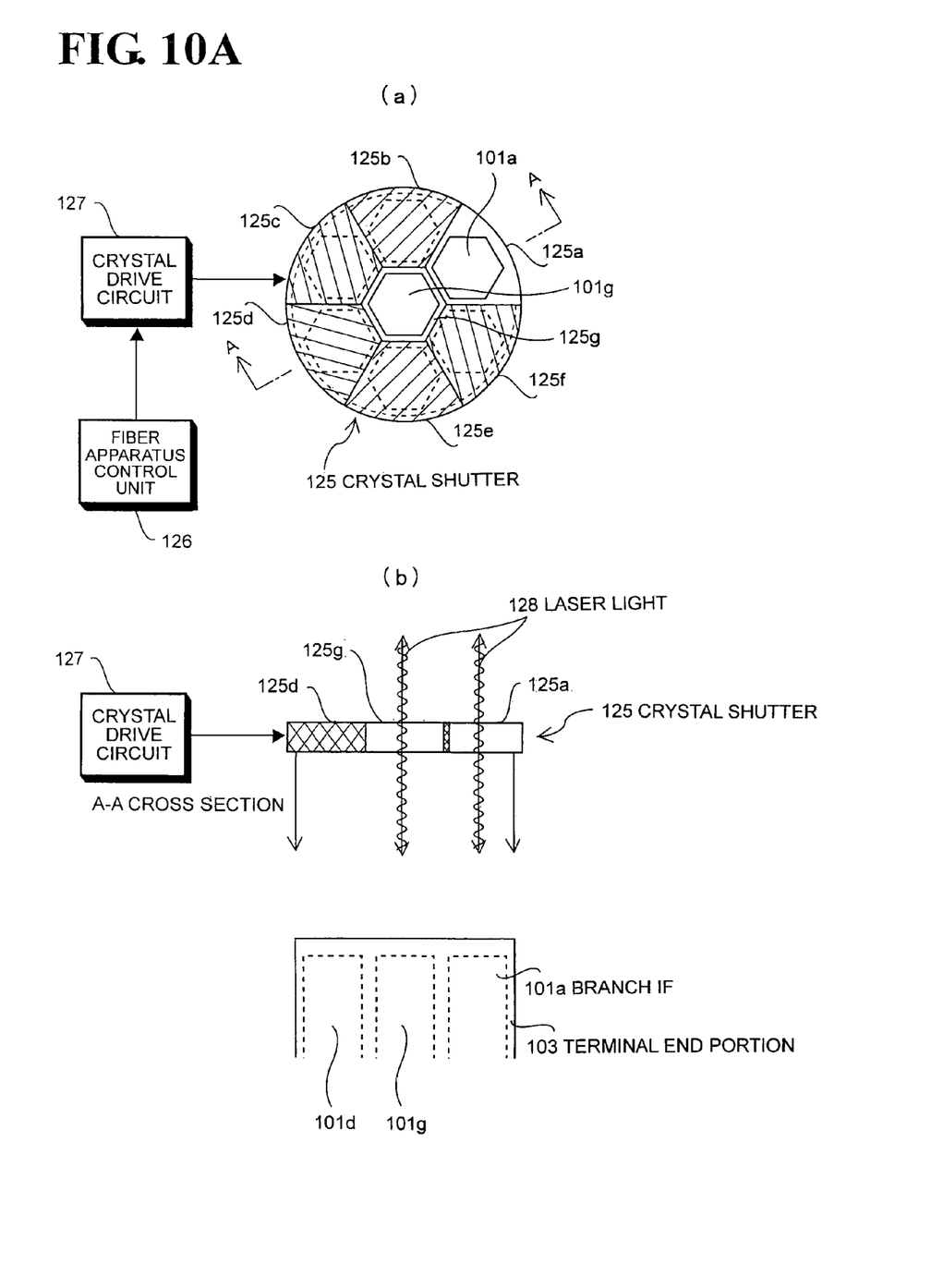
FIG. 10A is a diagram for explaining a configuration example of the crystal shutter.

FIG. 10A is a diagram for explaining a configuration example of the crystal shutter. In the present embodiment, crystal surfaces are switched on and off to correspond to the respective hexagonal openings of the seven branch IFs. A fiber apparatus control unit 126 outputs a signal for performing an ON-OFF control on the crystal surfaces corresponding to the openings of the respective branch IFs. In accordance with the control signal, a crystal drive circuit 127 performs an ON-OFF drive of the respective crystal surfaces. In the present example, to supply the light to the opening of the central branch IF 101g and the opening of the upper-right branch IF 101a, only crystal surfaces 125g and 125a are switched on, and the other crystal surfaces are controlled to be off. The light transmitted through the crystal surfaces 125g and 125a reaches the openings of the branch IFs 101g and 101a of the terminal end portion 103 via the lenses and the dichroic mirror.

Figure 10B:
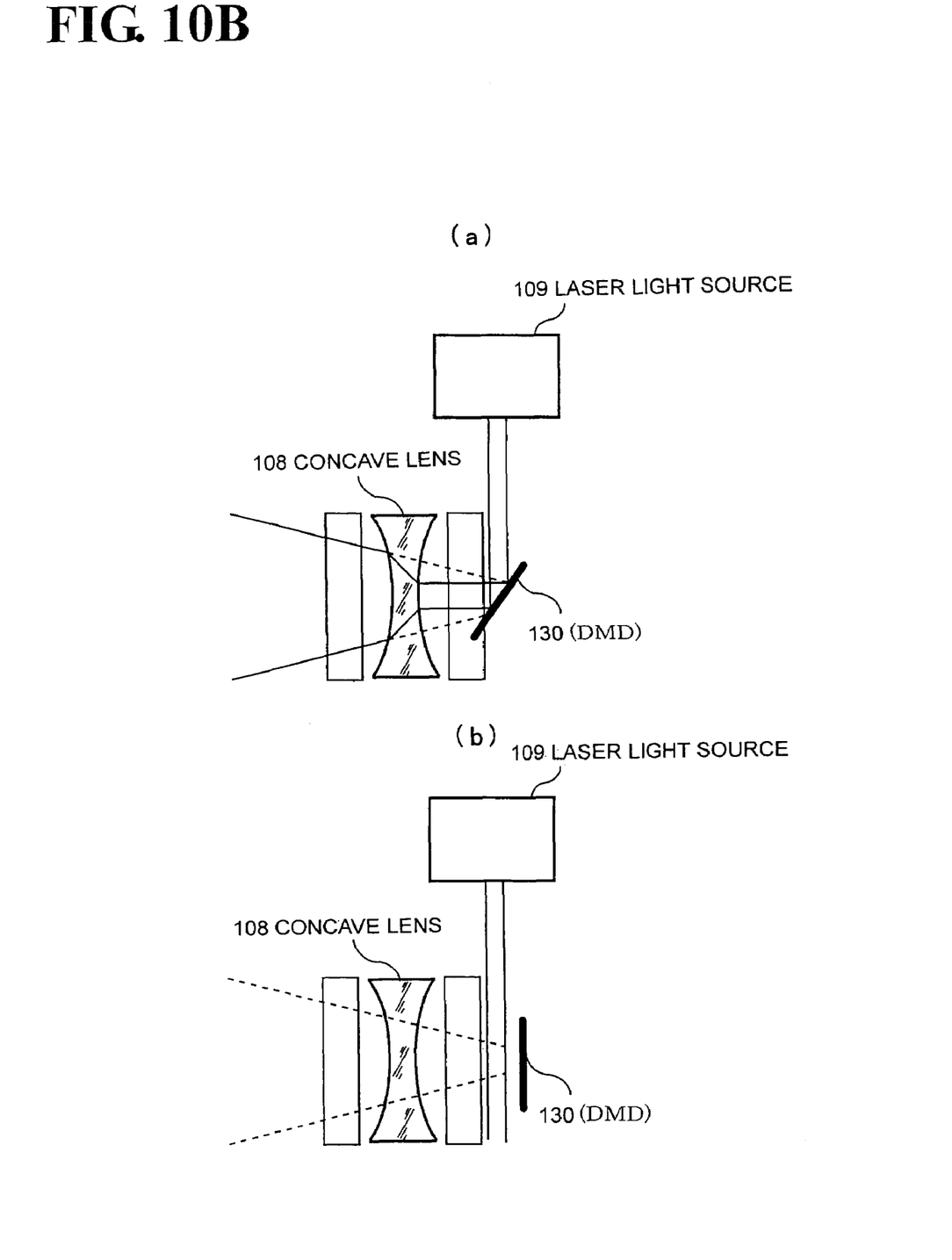
FIG. 10B is a diagram for explaining an example of control of the divided supply of light by a DMD.

FIG. 10B is a diagram for explaining an example of control of the divided supply of light by the DMD. The ON-OFF control of the incidence of light on the respective branch IFs is performed by the DMD. A DMD 130 is provided behind the concave lens 108 at the conjugate position with the terminal end portion 103, and the laser light source 109 is provided in the direction rotated by 90 degrees from the optical axis of the concave lens 108.

(a) of FIG. 10B illustrates the state in which the light output from the laser light source 109 is reflected to the concave lens 108 through the ON control by the DMD 130. In this case, the region of the DMD 130 which reflects the light is a region corresponding to the opening of the branch IF on which the light should be made incident. Therefore, the light can be supplied to all of the branch IFs at the same time or only a predetermined one of the branch IFs. In (b) of FIG. 10B, the openings of all of the branch IFs are not supplied with the light, i.e., the DMD 130 is in the OFF state.

Figure 10C:
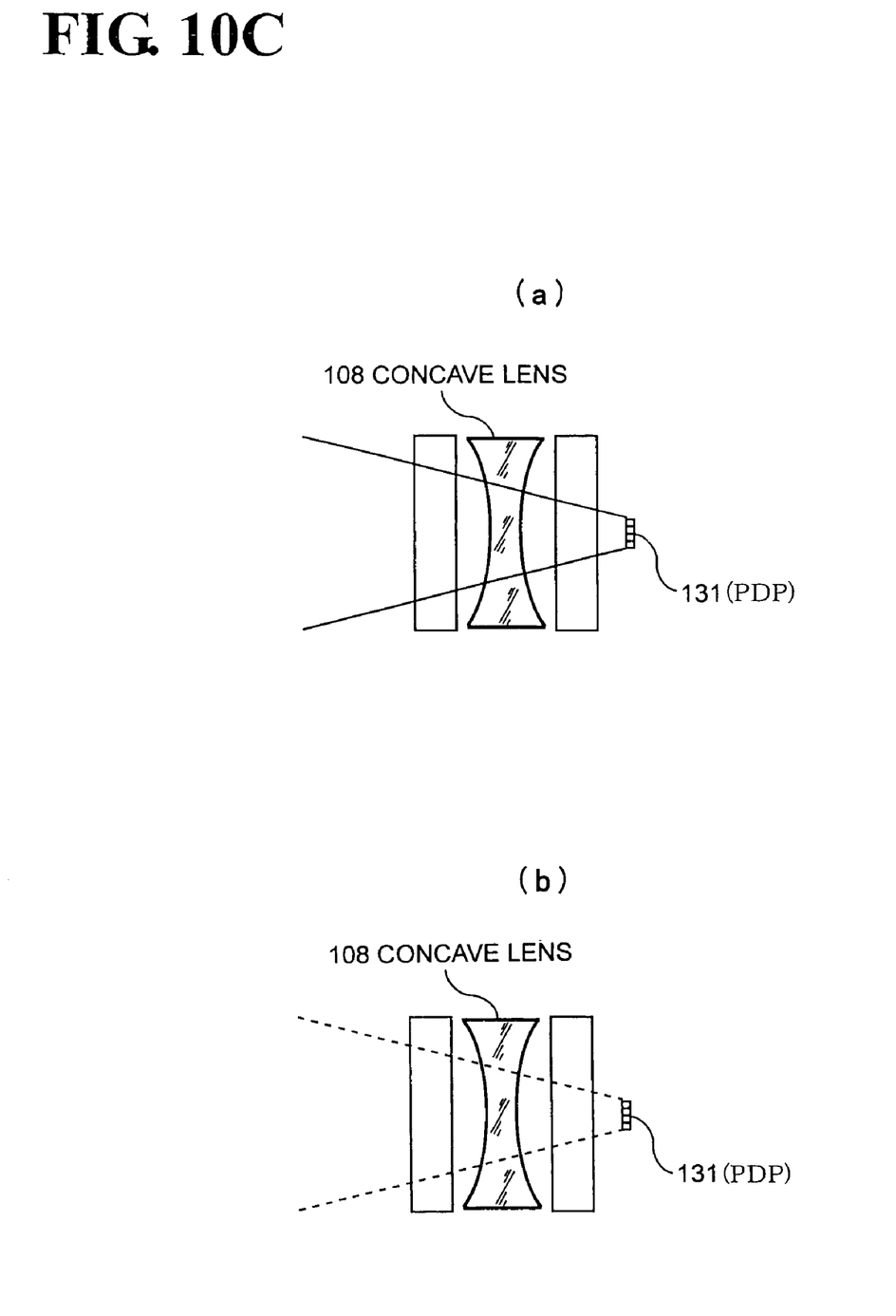
FIG. 10C is a diagram for explaining an example of control of the divided supply of light by a PDP.

FIG. 10C is a diagram for explaining an example of control of the divided supply of light by a PDP (plasma display), in which the PDP is used as the light source. A PDP 131 is provided behind the concave lens 108 at the conjugate position with the terminal end portion 103, and respective minute light emitting portions forming the PDP 131 are controlled by a signal to emit light. Respective light emitting areas formed by the multitude of minute light emitting portions correspond to the respective openings of the branch IFs on which the light should be made incident. (a) of FIG. 10C illustrates the state in which all of the respective light emitting areas are placed in the ON state, i.e., the light is applied to the openings of all of the branch IFs. It is also possible to place only a predetermined one of the light emitting areas in the ON state to supply the light to the opening of an arbitrary one of the branch IFs. In (b) of FIG. 10C, all of the minute light emitting portions of the PDP 131 are placed in the OFF state, and thus the light is not transmitted.

Figure 11:
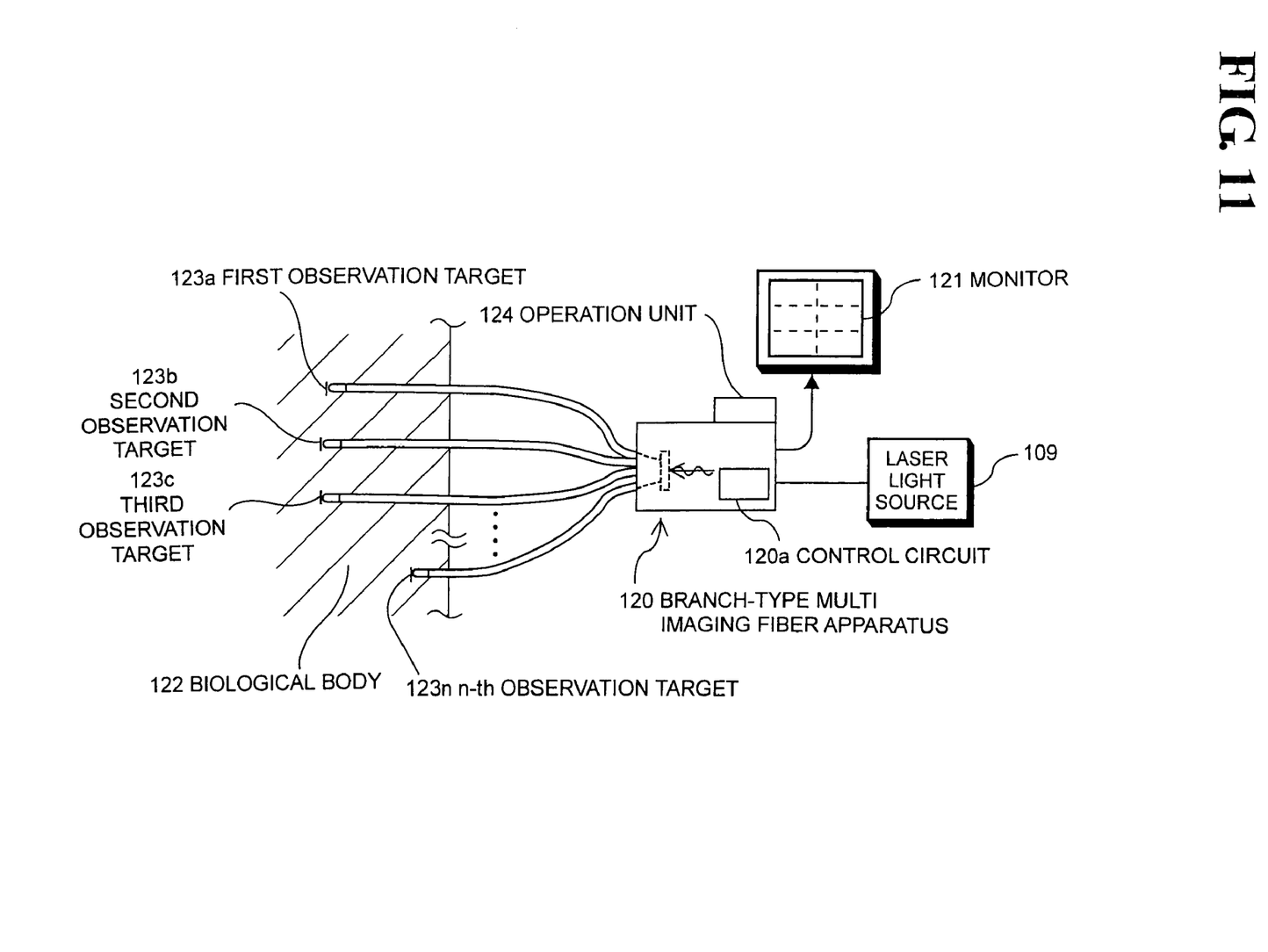
FIG. 11 is a diagram for explaining a use state of the branch-type imaging fiber apparatus according to the present invention.

FIG. 11 is a diagram for explaining a use state of the branch-type imaging fiber apparatus according to the present invention. A branch-type multi imaging fiber apparatus 120 stores the terminal end portion 103, and includes therein the first objective lens 105, the dichroic mirror 106, the collimator lens 107, the concave lens 108, the crystal shutter 104, the imaging lens 110, the image pickup device 111, and so forth. The output of the image pickup device 111 is connected to an image pickup device control unit provided in a control circuit 120a. Further, the branch-type multi imaging fiber apparatus 120 is connected to the laser light source 109 by an optical waveguide to guide the laser light to the crystal shutter 104. The branch-type multi imaging fiber apparatus 120 is further connected to a monitor 121.

An operation unit 124 includes a button switch, a slide switch, and so forth, and an operation signal output from the operation unit 124 is sent to the control circuit 120a. The control circuit 120a is a circuit for controlling the entirety of the branch-type multi imaging fiber apparatus 120, and includes a fiber apparatus control unit 126 and a crystal drive circuit 127. On the basis of the operation signal, the control circuit 120a performs an ON-OFF control of the monitor 121 and the laser light source 109, and controls the image display range of the monitor 121. Further, on the basis of a specification signal for specifying the branch IF to which the light should be supplied, the control circuit 120a controls the crystal shutter 104 to transmit the light through the opening of the specified branch IF.

The monitor 121 can display the images of the observation targets as divided images in accordance with the number of the specified branch IFs. The monitor 121 can further display each of the images on the entire screen thereof in a time-division manner. Accordingly, the multiple-point measurement can be performed by the single branch-type multi imaging fiber apparatus 120. The present example illustrates the state in which a biological body 122 is formed with holes at a plurality of (e.g., six) locations, and the branch IFs are inserted in the holes. Further, the light is applied to the first to n-th observation targets 123a to 123n, and the light emitted from the respective observation targets is received and image-processed by the image pickup device 111. Then, the images of the observation targets of the respective branch IFs are simultaneously observed on the screen of the monitor 29, which is divided into six sections.

The embodiment of FIG. 11 illustrates the example in which the plurality of locations in the biological body are observed by the single apparatus. It is also possible to observe an observation target existing at one location from different angles.

In the light blocking device described above, the crystal shutter, the DMD, or the PDP is used as an example. As well as the crystal shutter, the DMD, and the PDP, a multi-channel light source, such as an LED array, can be employed.

The present invention can be applied to a switch-type imaging fiber apparatus and a branch-type imaging fiber apparatus which insert imaging fibers into introduction holes or the like formed in a biological body, apply light to affected areas existing at a multitude of locations through the respective imaging fibers, and receive resultant reflected light to thereby enable observation of the affected areas by the single fiber apparatus.

What is claimed is:

1. A switch-type imaging fiber apparatus used to observe a biological body by applying light to an observation target from a leading end of the apparatus and receiving resultant reflected light, the apparatus comprising:
   a plurality of imaging fibers;
   a moving means for fixing end surfaces of the plurality of imaging fibers at predetermined intervals and capable of causing rotational movement of the end surfaces;
   a light source device; and
   an objective lens system for focusing light emitted from the light source device so as to form an irradiation surface approximately the same in area as the end surface of one of the plurality of imaging fibers,
   wherein, as the moving means is driven to move the end surface of the imaging fiber, the light emitted from the light source device is switched to be made incident among the end surfaces of the plurality of imaging fibers and the moving means is formed into a rotary revolving disk in which the end surfaces of the plurality of imaging fibers are circumferentially arranged and rotated.

2. The switch-type imaging fiber apparatus according to claim 1, wherein each of the imaging fibers is formed by a few thousands to a few tens of thousands of fiber strands.

3. The switch-type imaging fiber apparatus according to claim 1, wherein each of the plurality of imaging fibers includes an opening, and the openings are arranged circumferentially around the rotary revolving disk at equal intervals.

4. The switch-type imaging fiber apparatus according to claim 1, wherein the rotary revolving disk is controlled to rotate by an angle not exceeding 180 degrees in a clockwise direction or in a counterclockwise direction.

5. The switch-type imaging fiber apparatus according to claim 1, wherein the materials forming the imaging fibers are flexible.

6. A switch-type imaging fiber apparatus used to observe a biological body by applying light to an observation target from a leading end of the apparatus and receiving resultant reflected light, the apparatus comprising:
   a plurality of imaging fibers;
   a moving means for fixing end surfaces of the plurality of imaging fibers at predetermined intervals and capable of causing linear movement of the end surfaces;
   a light source device; and
   an objective lens system for focusing light emitted from the light source device so as to form an irradiation surface approximately the same in area as the end surface of one of the plurality of imaging fibers,
   wherein the moving means is formed into a belt conveyance system in which the end surfaces are attached to a belt in a row and the belt is driven.

* * * * *